United States Patent [19]

Callaghan et al.

[11] Patent Number: 5,589,196
[45] Date of Patent: Dec. 31, 1996

[54] ANTIPERSPIRANT COMPOSITION

[75] Inventors: David T. Callaghan, Quincy; Alan M. Phipps, Framingham, both of Mass.; Stephen J. Provancal, Addison, Ill.

[73] Assignee: The Gillette Company, Boston, Mass.

[21] Appl. No.: 252,376

[22] Filed: Jun. 1, 1994

Related U.S. Application Data

[60] Continuation of Ser. No. 846,016, Mar. 4, 1992, abandoned, which is a division of Ser. No. 287,096, Dec. 20, 1988, Pat. No. 5,114,705, which is a continuation of Ser. No. 713,470, Mar. 19, 1985, abandoned, which is a continuation-in-part of Ser. No. 523,785, Aug. 16, 1983, abandoned.

[51] Int. Cl.$^6$ .............. A61K 33/24; A61K 7/32; C01G 25/00; C01F 7/00
[52] U.S. Cl. .............. 424/617; 252/182.33; 252/182.35; 423/608; 423/625; 424/65; 424/66; 424/68; 424/600
[58] Field of Search .............. 424/63, 66, 68, 424/600, 617; 252/182.33, 182.35; 423/608, 625

[56] References Cited

U.S. PATENT DOCUMENTS

| 2,854,382 | 9/1958 | Grad | 424/66 |
|---|---|---|---|
| 2,906,668 | 9/1959 | Beekman | 424/66 |
| 4,359,456 | 11/1982 | Gosling | 424/68 |
| 4,435,382 | 3/1984 | Shin | 424/66 |

FOREIGN PATENT DOCUMENTS

| 0047650 | 3/1982 | European Pat. Off. | 424/66 |
|---|---|---|---|
| 0070517 | 1/1983 | European Pat. Off. | 424/66 |
| 2537359 | 3/1976 | Germany | 424/66 |
| 835385 | 5/1960 | United Kingdom | 424/66 |
| 1353916 | 5/1974 | United Kingdom | 424/66 |
| 2048229 | 4/1980 | United Kingdom | 424/66 |
| 2076289 | 12/1981 | United Kingdom | 424/66 |
| 2144992 | 3/1985 | United Kingdom | 424/66 |

*Primary Examiner*—Shelley A. Dodson
*Attorney, Agent, or Firm*—Stephan P. Williams

[57] ABSTRACT

A composition of zirconyl hydroxy chloride and aluminum chlorhydroxide in stable solid form having improved antiperspirant efficacy when dissolved in water is made by heating a 2–20% by weight aqueous solution containing at least the aluminum chlorhydroxide component of the composition at a temperature of at least 50° C. until the ratio of the height of peak 4 at Kd=0.7 to that of peak 3 at Kd=0.5 as measured by gel permeation chromatography on crosslinked dextran is at least 2:1, then subjecting the solution to rapid drying to solid form.

32 Claims, 4 Drawing Sheets

ANTIPERSPIRANT COMPOSITION

This application is a continuation of Ser. No. 07/846,016 filed Mar. 4, 1992, now abandoned, which is a division of Ser. No. 07/287,096 filed Dec. 20, 1988, now U.S. Pat. No. 5,114,705, which is a continuation of Ser. No. 06/713,470 filed Mar. 19, 1985, now abandoned, which is a continuation-in-part of Ser. No. 06/523,785 filed on Aug. 16, 1983, now abandoned.

This invention relates to improving the antiperspirant effectiveness of compositions comprising zirconyl hydroxy chloride and aluminum chlorhydroxide and to such improved compositions in solid stable form.

It has hitherto been proposed to increase the antiperspirant effectiveness of aluminum chlorhydroxide by aging under specified conditions an aqueous solution containing the aluminum chlorhydroxide, as described in Gosling et al. U.S. Pat. No. 4,359,456 and in British Patent Application No. 2,048,229A until the solution exhibits specified characteristics. In the British application, it is pointed out that the increased activity is the result of a group of complexes called $Al^{c'}$ characterized by having a diffusion constant in gel permeation chromatography which is within the range generally found for the $Al^b$ group of complexes but which displays a complexing rate in the ferron test which is in the range of the $Al^c$ complexes and by having molecules which are less than 100 A in size in aqueous solution. The $Al^{c'}$ complexes thus prepared are stable in aqueous solution at concentrations in the range 10% to 30%.

It has now been found that a composition comprising zirconyl hydroxy chloride and aluminum chlorhydroxide, unlike aluminum chlorhydroxide alone, does not form a stable aqueous solution when heated, but that a different molecular complex displaying increased antiperspirant effectiveness is formed by heating an aqueous solution containing at least the aluminum chlorhydroxide component and mixing with it the zirconium hydroxy chloride component. The zirconium hydroxy chloride may be present initially or can be added at any time during or after heating. The novel complex, of lower molecular weight than $Al^{c'}$, contains no zirconium, and reverts rapidly in aqueous solution at room temperature to one containing less of the novel complex, losing approximately ½ of its initial concentration in 48 hours. The composition containing the novel complex as described herein displays improved antiperspirant efficacy as compared to an aqueous solution made by dissolving conventional zirconyl hydroxy chloride and aluminum chlorhydroxide in water or as compared to conventional commercially available aqueous solutions containing the zirconyl and aluminum compounds. The novel complex can be formed at least in part from the higher molecular weight $Al^{c'}$ complex of the prior art and is segregated in a separate zone from $Al^{c'}$ when the aqueous solution is subjected to gel permeation chromatography. When the aqueous solution containing both aluminum chlorhydroxide and zirconyl hydroxy chloride is subjected to heating, the $Al^{c'}$ complex initially present in the solution gradually decreases in amount while at the same time the amount of the novel complex present gradually increases. An aqueous solution containing the novel complex of the present invention in large amount is unstable at room temperature, as stated above, and the amount of the novel complex present in such a solution decreases quite rapidly while the amount of $Al^{c'}$ increases. Because of this inherent instability, aqueous solutions of zirconyl hydroxy chloride and aluminum chlorhydroxide containing the novel complex of the present invention cannot be used as such as a commercially practical antiperspirant. However, it has been found that if the aqueous solution containing the novel complex is rapidly solidified by removal of water, the solid product retains in large part the desired complex and its high antiperspirant effectiveness. The solid product consequently can be employed as an antiperspirant in finely-divided form, e.g. in a powder either alone or with a diluent powder vehicle such as talc, or in the form of a cream or suspension in a non-aqueous liquid vehicle, for example a high viscosity cream for manual application, a low viscosity suspension for roll-on application, or a suspension in a liquefied propellant for aerosol application. Any conventional non-aqueous physiologically and cosmetically acceptable non-toxic vehicle can be used with the particulate solid composition of the present invention to form an antiperspirant composition. Particle size may vary over a wide range but preferably is from 1 to 100 micrometers in diameter. Relative proportions of vehicle and particulate solid are not critical. In general, the weight of particulate solid may range from 0.1 to 80% or more of the total weight of the composition including vehicle. After the finely-divided solid comes into contact with the skin, it dissolves in the initial perspiration present on the skin and becomes effective as an antiperspirant.

The present invention comprises a stable solid composition comprising zirconyl hydroxy chloride and aluminum chlorhydroxide in which the atomic ratio of Al to Zr is from 6:1 to 1:1 having high antiperspirant efficacy, said composition, when dissolved in water to form a 10% by weight solution and, after storage at room temperature for no more than 2 hours, subjected to gel permeation chromatography on cross-linked dextran having a molecular weight exclusion range of 1000 to 30,000 for globular proteins (Sephadex G-50), exhibits a distribution pattern having peaks at $Kd=0.7$ and $Kd=0.5$ in which the ratio of the height of the first peak to that of the second is at least 1.5:1.

All of the chromatograms referred to herein are obtained by passing aqueous solutions at 10% concentration through the specified cross-linked dextran column, employing as eluent 0.1 molar aqueous KCl adjusted to pH3 with HCl, and monitoring the refractive index of the eluent.

The invention also comprises the method of making an antiperspirant composition having high efficacy which comprises providing a 2% to 18% solution of aluminum chlorhydroxide in water, heating the solution at a temperature of at least 50° C., mixing zirconyl hydroxy chloride with the solution before, during or after said heating step, the amount of said zirconyl compound being sufficient to provide an atomic ratio of Al:Zr from 6:1 to 1:1, said heating being continued until measurement by gel permeation chromatography of said solution at a concentration of 10% on cross-linked dextran having a molecular weight exclusion range of 1000 to 30,000 for globular proteins shows peaks at $Kd=0.7$ and $Kd=0.5$ and the ratio of the first peak to the second is at least 2:1, and at least 80%, preferably at least 90%, of the total aluminum is present within said peaks, and subjecting said solution to rapid drying to solid form, said solid, when dissolved in water to form a 10% by weight solution and, after storage at room temperature for no more than two hours, subjected to gel permeation chromatography on said cross-linked dextran exhibiting a distribution pattern having peaks at $Kd=0.7$ and at $Kd=0.5$ in which the ratio of the height of the first peak to that of the second peak is at least 1.5:1, preferably at least 2:1. The amount of zirconyl hydroxy chloride added is such that the mixed solution contains 2 to 20% by weight of total solids; the zirconyl hydroxy chloride may be mixed with the solution after drying has begun and before viscosity has increased to the point where mixing is difficult and must be mixed with it before the solution has been completely dried. The zirconyl hydroxy chloride can be in solid form or in aqueous solution when mixed with the aluminum chlorhydroxide; when mixed with the solution after drying has begun, the zirconium hydroxy chloride is preferably introduced in the form of an aqueous solution, preferably at a concentration of 30% to 55%; it may contain an amino acid such as glycine. The mixing may be carried out at room temperature or at elevated temperatures up to the maximum temperature at which the heating is conducted. Although heating of the aluminum chlorhydroxide solution, with or without the addition of the zirconyl hydroxy chloride, is required to produce the desired new complex in substantial amount, once the necessary heating has been completed without addition of the zirconyl compound the desired complex forms very rapidly after the introduction of the zirconyl compound. The invention also comprises the method of increasing the antiperspirant efficacy of a composition comprising zirconyl hydroxy chloride and aluminum chlorhydroxide which comprises providing a 2% to 20% solution in water of such composition in which the atomic ratio of Al to Zr is from 6:1 to 1:1, heating the solution at a temperature of at least 50° C. until the ratio of the height of a peak at $Kd=0.7$ to that of a peak at $Kd=0.5$ as measured by gel permeation chromatography of a 10% aqueous solution on cross-linked dextran having a molecular weight exclusion range of 1000 to 30,000 for globular proteins is at least 2:1, then subjecting the solution to rapid drying to solid form, said solid, when dissolved in water to form a 10% by weight solution and subjected to gel permeation chromatography on said cross-linked dextran after storage at room temperature for no more than 2 hours, exhibiting a distribution pattern having peaks at $Kd=0.7$ and at $Kd=0.5$ in which the ratio of the height of the first to that of the second peak is at least 1.5:1, preferably at least 2:1.

In the appended drawings,

FIG. 1 represents a chromatogram of a freshly prepared 10% by weight aqueous solution of zirconyl hydroxy chloride and aluminum chlorhydroxide;

FIG. 2 represents a chromatogram of the solution of FIG. 1 after heating at 100° C. for 2 hours; peak 4 is at $Kd=0.7$ and peak 3 is at $Kd=0.5$;

Figure 5:
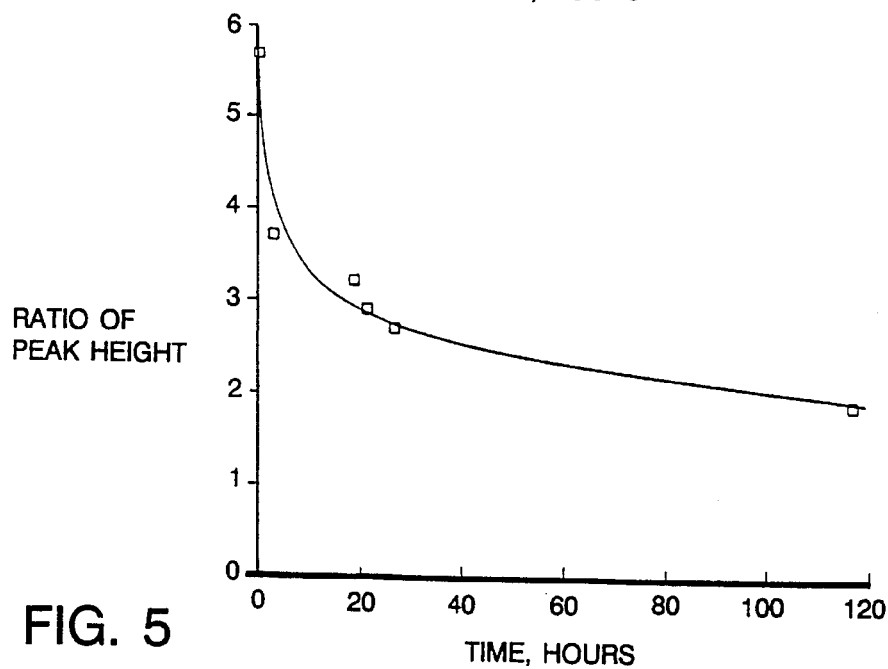
Figure 6A:
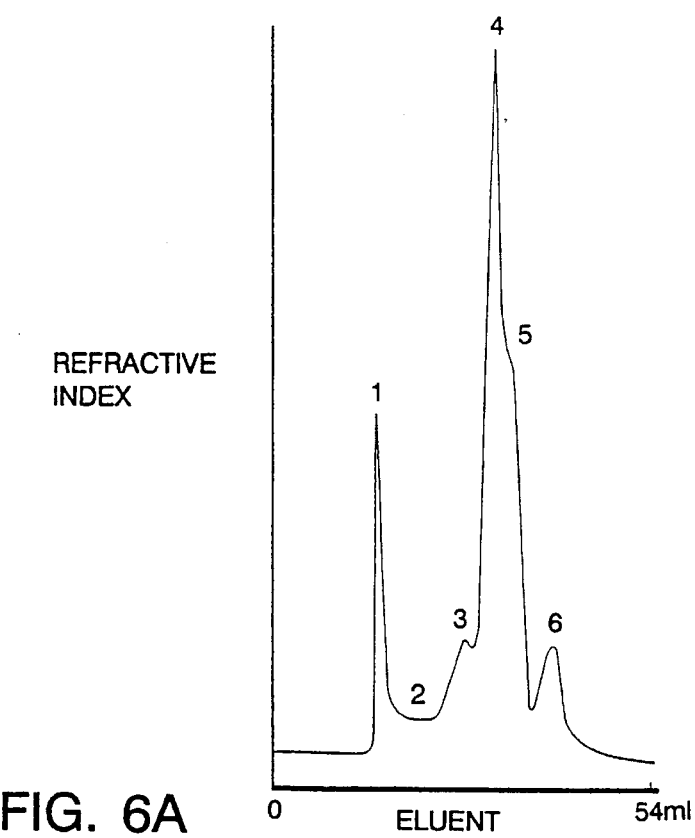
Figure 6B:
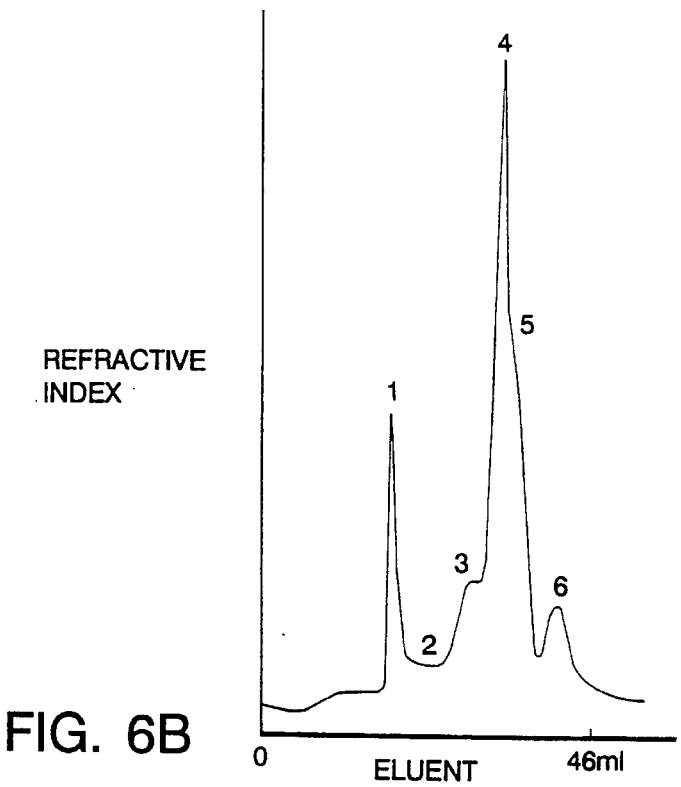
Figure 7A:
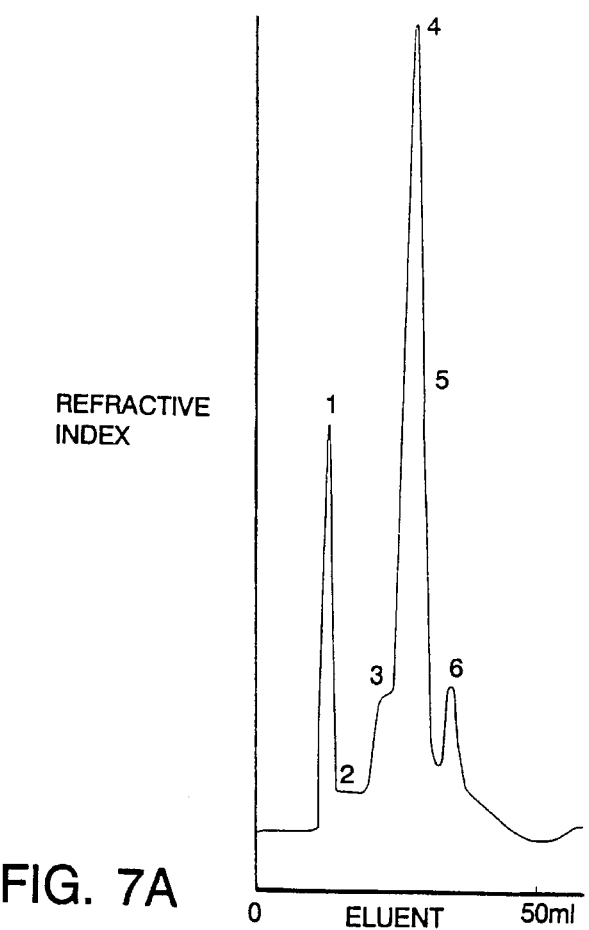
Figure 7B:
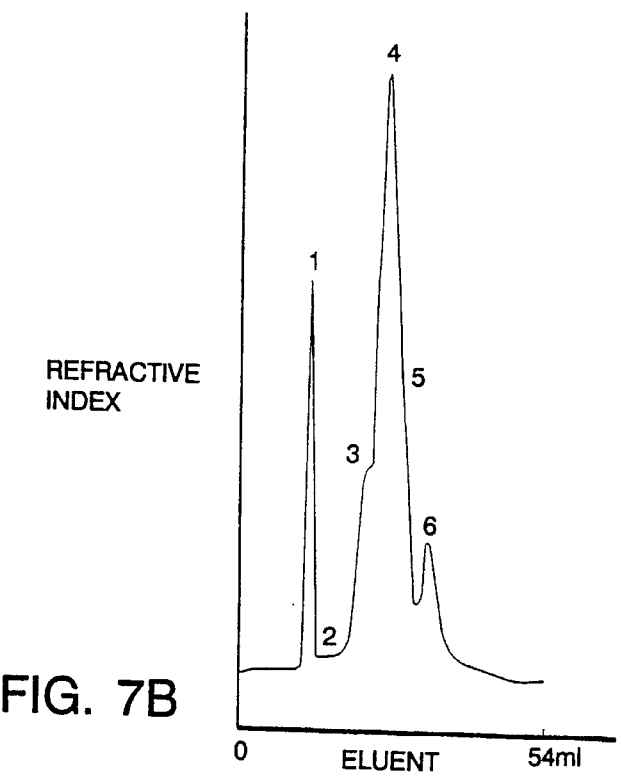

FIG. 5 is a plot showing the ratio of heights of peak 4 ($Kd=0.7$) to peak 3 ($Kd=0.5$) during room temperature storage of the aluminum and zirconium compounds after previously heating at 100° C. for 46 hours;

FIG. 6a shows the chromatogram of a 10% aqueous solution of a mixture of zirconium and aluminum compounds of the present invention after heating at 100° C. for 20 hours; peak 4 is at $Kd=0.7$ and peak 3 is at $Kd=0.5$;

FIG. 6b is a chromatogram of a 10% aqueous solution of the solid made by spray-drying the solution of FIG. 6a; peaks 4 and 3 are as stated in FIG. 6a;

FIG. 7 is a chromatogram of a 10% aqueous solution of the zirconium and aluminum compounds of the present invention after heating at 100° C. for 17 hours; peak 4 is at $Kd=0.7$ and peak 3 is at $Kd=0.5$;

FIG. 7b is a chromatogram of a 10% aqueous solution of the solid product made by freeze-drying the solution of FIG. 7a; peaks 4 and 3 are as stated in FIG. 7a;

The compositions of zirconyl hydroxy chloride and aluminum chlorhydroxide which can be employed in the present invention include those in which the zirconyl compound has the formula $ZrO(OH)_xCl_y$ where $X+Y=2$ or a hydrate thereof and the aluminum compound has the formula $Al_2(OH)_{6-n}Cl_n$ where n is from 0.8 to 2 or a hydrate thereof, n preferably being 1. The atomic proportion of aluminum to zirconium in the composition may vary from about 1:1 to 6:1. The atomic proportion of metal to chloride may vary from about 0.9 to 1.9. The inclusion in the composition of a neutral amino acid as described in Grad U.S. Pat. No. 2,854,382, which patent is incorporated herein by reference, does not have an adverse effect upon the formation of the desired novel complex. Commercially available compositions of zirconyl hydroxy chloride and aluminum chlorhydroxide mixtures frequently contain glycine as the neutral amino acid in an amount such that the molar ratio of glycine to zirconyl hydroxy chloride is about 1:1. The glycine or other neutral amino acid aids in preventing gelation of the aqueous solution before or during the heating step of the method of the present invention; and its presence does not prevent formation of the desired complex and does not interfere with the conversion of the heated solution to solid form nor with the subsequent use of the solid as an antiperspirant. Solid compositions as well as aqueous solutions containing zirconyl hydroxy chloride and aluminum chlorhydroxide are available commercially, usually containing a water solution amino acid to prevent gelling; these materials may be employed in practicing the present invention. The individual zirconyl and aluminum components can also be obtained commercially and mixed in solution.

It is preferred for best results to make the composition by employing as starting material an aqueous solution containing aluminum chlorhydroxide at a concentration of 8% to 15% by weight (all concentrations hereinafter are by weight) to which is added after the desired heating an amount of zirconyl hydroxy chloride containing an approximately equimolar quantity of glycine, the amount of zirconyl compound being sufficient to provide an atomic ratio of Al to Zr equal to about 4:1. It is essential that the solution containing the desired complex be dried rapidly to solid form; preferably, the zirconium compound is added to the solution after drying has begun but before the solution becomes so concentrated that mixing is difficult; for example, the finely divided solid zirconium hydroxy chloride monoglycinate can be mixed with the solution when it has been partially dried to a concentration of 45%–55% by thin film vacuum flash evaporation, and after dissolution is complete drying can be completed by spray drying to solid form. The extent of heating of the aluminum chlorhydroxide solution before addition of the zirconyl compound is optional, but in the preferred embodiment it is heated at a temperature of at least 50° C., preferably 70° to 100°, to the extent that no further heating after addition of the zirconyl compound (except for whatever heat is needed for drying) is required to form the desired complex. Although temperatures above 100° C. can be used, pressure vessels are needed for higher temperatures adding to the expense, so that temperatures from 70° C. to 100° C. are most preferred. When the heating is carried out at 80° C. using a 10% aqueous solution, approximately 16 hours heating is required. If the heating of the aluminum chlorhydroxide solution is insufficient to achieve the specified condition before the zirconyl hydroxy chloride is mixed with it, the solution containing both the aluminum and the zirconyl compound can be heated to achieve the desired result.

In the case where there has been no heating of the aluminum chlorhydroxide solution before adding the zirconyl compound to it, the complex of the invention can be made by providing an aqueous solution containing a mixture of zirconyl hydroxy chloride and aluminum chlorhydroxide in an amount from about 2% to about 20% by weight of the total solution, preferably 8 to 15%, and heating it at a temperature of at least 50° C., preferably 70° C. or higher. After heating has been continued for several hours an aliquot sample of the solution is subjected to gel permeation chromatography on a cross-linked dextran, (Sephadex G-50) using as the eluent 0.1 molar aqueous KCl with the pH adjusted to 3.0 with HCl; and the distribution of the metal complexes is measured by monitoring the refractive index of the eluent. As appears from FIG. 1, 6 peaks occur in the case of a typical freshly prepared 10% by weight aqueous solution containing zirconyl hydroxy chloride and aluminum chlorhydroxide $(Al)_2(OH)_5Cl$. Peak 1 as shown in the drawing is the eluent fraction containing the zirconium compound; this compound is excluded by the gel because of its large molecular size. Peak 2 contains the $Al^c$ complex, and peak 3, at Kd=0.5 contains the $Al^{c'}$ complex. Peak 4 at Kd=0.7, which appears only as a shoulder between peaks 3 and 5 contains The hitherto unrecognized novel complex which is present only in small proportion, while peaks 5 and 6 are fractions containing $Al^a$ or other lower molecular weight compounds.

Figure 1:
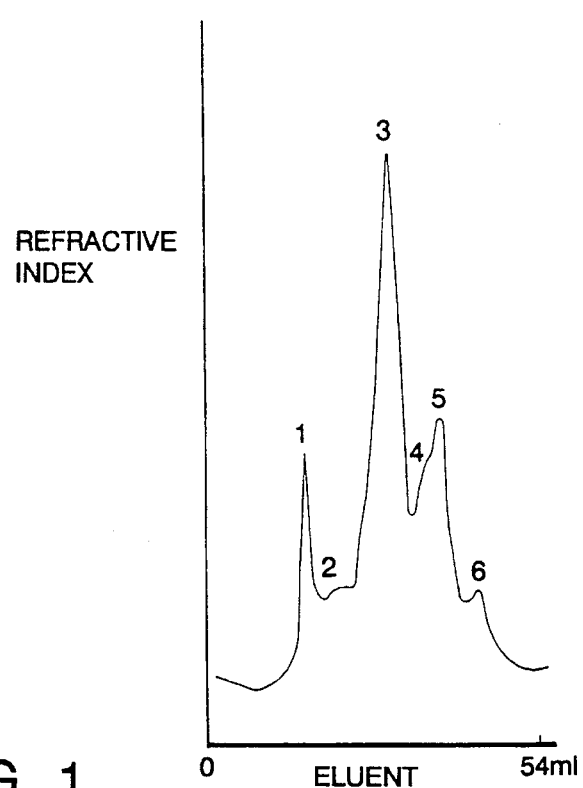
Figure 2:
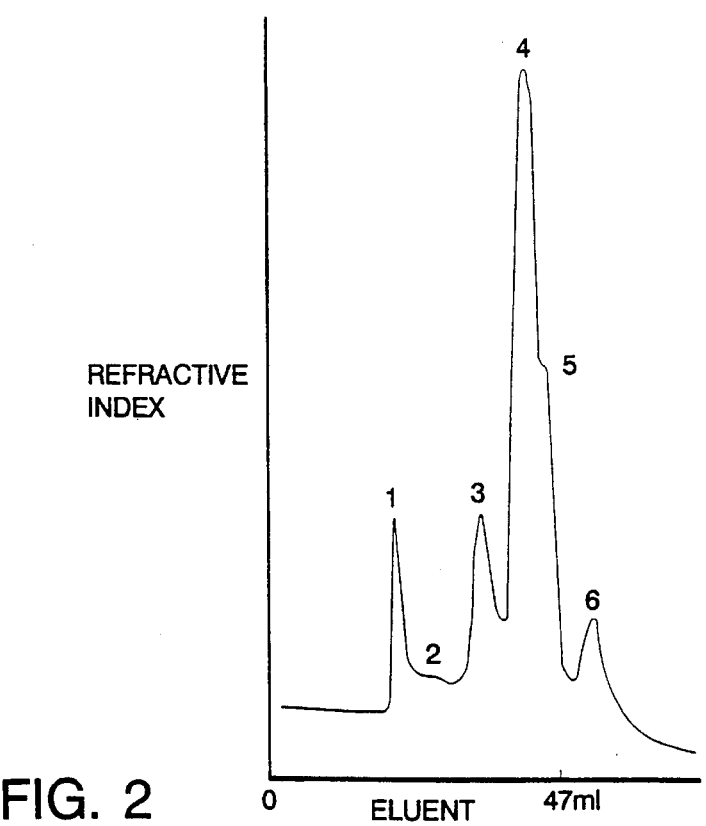

As appears from FIG. 2 of the drawing, the solution characterized in FIG. 1, after heating at 100° C. for 2 hours, displays a quite different distribution of complexes when subjected to gel permeation chromatography under the same conditions, the most striking change being a large decrease in the height of peak 3 at Kd=0.5 and a very large increase in the height of peak 4 at Kd=0.7. It has been found that the extent of antiperspirant efficacy of the composition is generally proportional to the relative heights of peak 4 and peak 3, i.e. to the relative amounts of the complex of peak 4 at Kd=0.7 present in the composition as compared to the $Al^{c'}$ complex of peak 3 at Kd=0.5. Those compositions in which the ratio of the height of peak 4 to that of peak 3 is at least 1.5:1, preferably at least 2:1 display the desired superior antiperspirant efficacy.

The length of time of heating necessary to achieve the desired ratio of height of peak 4 at Kd=0.7 to peak 3 at Kd=0.5 depends upon the temperature and the concentration of the solution. The higher the temperature, the more rapid is the increase in ratio. To achieve a ratio of height of peak 4 to peak 3 of 3 or more, it is necessary to heat solutions of a concentration of 2–10% at a temperature of 80° C. or more.

Figure 3:
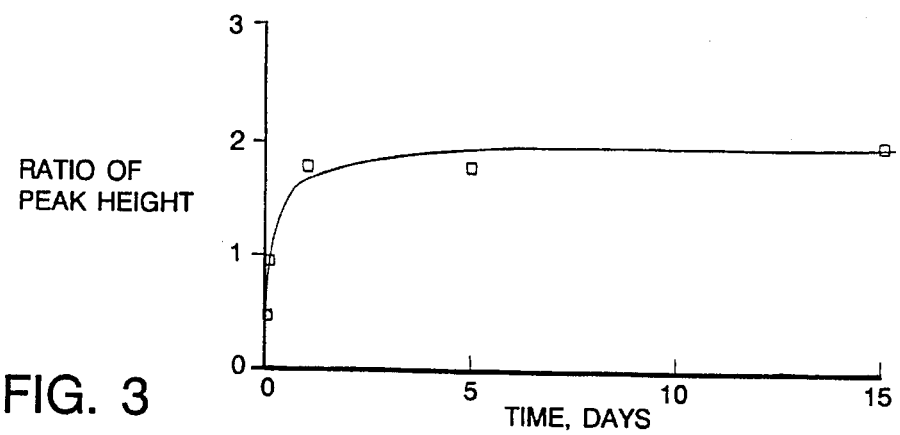
FIG. 3 is a plot showing the ratio of the heights of peak 4 ($Kd=0.7$) to peak 3 ($Kd=0.5$) of chromatograms of a 10% aqueous solution of the aluminum and zirconium compounds heated for varying time periods at 50° C.
Figure 4:
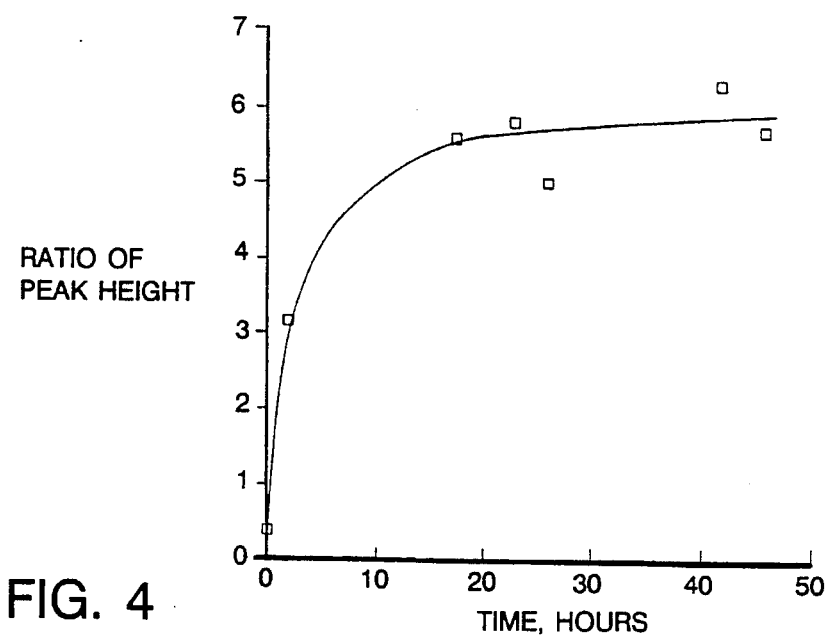
FIG. 4 is a plot showing the ratio of the heights of peak 4 ($Kd=0.7$) to peak 3 ($Kd=0.5$) of chromatograms of the solution of FIG. 1 when heated at reflux for varying time periods.

In the case of a 10% aqueous solution heated at 50° C., as shown in FIG. 3 of the drawing, the ratio of the height of peak 4 at Kd=0.7 to that of peak 3 at Kd=0.5 rapidly exceeds 1:1 and approaches a maximum of about 2:1 and thereafter remains substantially constant as heating is continued. This is typical of the results obtained at other temperatures and concentrations, as can be seen from FIG. 4 of the drawing which shows the change in the ratio of peak 4 to peak 3 of a 10% aqueous solution when heated at reflux temperature.

The rate of reversion at room temperature of a 10% aqueous solution which had previously been heated at 100° C. for 46 hours is shown in FIG. 5 of the drawing, from which it is clear that the ratio of reversion is so rapid that it is not commercially practical to package for sale aqueous solutions having a high ratio of peak 4 at Kd=0.7 to peak 3 at Kd=0.5.

The following specific examples are intended to illustrate more fully the nature of the present invention without acting as a limitation upon its scope.

EXAMPLE 1

Approximately 1 liter of an aqueous solution containing (10% solids) $ZrO(OH)Cl$, $Al_2(OH)_5Cl$ and glycine in which the atomic ratio of Al to Zr was 3.6 to 1 and the ratio of Zr to glycine was 1:1 was heated at 100° C. for 20 hours.

A portion of the solution, within less than 2 hours after cooling to room temperature, was subjected to gel permeation chromatography on a cross-linked dextran (Sephadex G-50) column using pH 3, 0.1M KCl as the eluent, and the refractive index of the eluent fractions was measured. The resulting chromatogram is shown in FIG. 6a. It exhibits successive peaks in which the height of peak 4 at Kd=0.7 is several times the height of pedak 3 at Kd=0.5, similar to that of FIG. 2.

Another portion of this heated solution was immediately subjected to spray-drying on a Buchi model 190 spray drier with an inlet temperature of 147° C. and an outlet temperature of 80° C. to provide a fine, dry powder.

A portion of the powder was then redissolved in water to form a 10% by weight solution and within less than 2 hours was subjected to gel permeation chromatography under the same conditions as the earlier solution. The resultant chromatogram is shown in FIG. 6b of the drawing, from which it is clear that the ratio of the height of peak 4 at Kd=0.7 to that of peak 3 at Kd=0.5 was not greatly changed.

EXAMPLE 2

A different specimen of a 10% aqueous solution of the same mixture of zirconyl, aluminum and glycine compounds was aged 17 hours at 100° C.; its gel permeation chromatographic characteristics, measured as in Example 1, are shown in FIG. 7a of the drawing. A specimen of the aged solution was immediately subjected to freeze-drying using a Virtis Unitrap Freeze-Drier. The dried residue was ground and passed through a 200 mesh sieve.

A portion of the powder was then redissolved in water to form a 10% by weight solution and subjected to gel permeation chromatography under the same conditions as the earlier solution. The resultant chromatogram is shown in FIG. 7b of the drawing. The slight reduction in ratio of height of peak 4 at Kd=0.7 to that of peak 3 at Kd=0.5 after freeze-drying while somewhat greater than the reduction which occurred in the case of spray-drying, still produced a product having enhanced antiperspirant activity as compared to the antiperspirant activity of the original aqueous solution characterized in FIG. 1 of the drawing.

Both the spray-dried and the freeze-dried solid powders exhibited no further substantial change in chromatographic characteristics during storage at room temperature for several months.

Typical antiperspirant formulations in which the material of the present invention may be practically employed are as follows:

|  | Weight % |
|---|---|
| I. Non-aqueous Roll-On | |
| Finely divided solid of present invention | 20.0 |
| Quaternium-18 Hectorite | 2.7 |
| Anhydrous Alcohol SDA-40 | 1.6 |
| $H_2O$ | 0.2 |
| Cyclomethicone, a silicone oil | 75.5 |

-continued

| | Weight % |
|---|---|
| Perfume | q.s. |
| II. Stick Antiperspirant | |
| Finely divided solid of present invention | 23.0 |
| Ozokerite Wax | 22.4 |
| Myristyl Alcohol | 17.2 |
| Cyclomethicone | 17.9 |
| PPG-15 Stearyl ether | 11.5 |
| Steareth-15 | 2.3 |
| Bentone Gel IPM | 5.7 |
| Perfume | q.s. |
| III. Aerosol Antiperspirant | |
| Finely divided solid of present invention | 7.0 |
| Talc | 2.0 |
| Anhydrous Alcohol SDA-40 | 4.2 |
| Quaternium-18 Hectorite | 1.4 |
| Cyclomethicone | 4.0 |
| Isopropyl myristate | 3.0 |
| Perfume | 0.1 |
| Propellant-A31 | 78.3 |

The product of the present invention has been evaluated for antiperspirant activity using standard Hot Room clinical testing procedures both as a 10% aqueous solution, and as a dry powder in a non-aqueous roll-on formulation. In each case, it was found to be superior to the analogous conventional material having the gel permeation characteristics as shown in FIG. 1 of the drawing.

What is claimed is:

1. An intermediate for making an antiperspirant composition having high efficacy, said intermediate comprising an aqueous solution of aluminum chlorhydroxide and zirconyl hydroxy chloride, the atomic ratio of Al to Zr being from 6:1 to 1:1, said solution, when stored at room temperature for no more than two hours and subjected to gel permeation chromatography at a concentration of 10% on cross-linked dextran having a molecular weight exclusion range of 1000 to 30,000 for globular proteins, showing a first peak at $Kd=0.7$ and a second peak at $Kd=0.5$, the ratio of the height of said first peak to that of said second peak being at least 1.5:1.

2. The intermediate of claim 1 in which the ratio of said peak heights is at least 2:1.

3. The intermediate of claim 1 in which at least eighty percent of the aluminum is present within said first and second peaks.

4. The intermediate of claim 3 in which said aluminum chlorhydroxide has a concentration of 2 to 18% in said solution.

5. The intermediate of claim 4 in which said solution contains a water-soluble amino acid.

6. The intermediate of claim 5 in which at least ninety percent of the aluminum is present within said first and second peaks.

7. The intermediate of claim 6 in which said aluminum chlorhydroxide has a concentration of 8 to 15% in said solution.

8. The intermediate of claim 6 in which said aluminum chlorhydroxide has a concentration of 2 to 18% in said solution.

9. The intermediate of claim 8 in which at least eighty percent of the aluminum is present within said first and second peaks.

10. The intermediate of claim 9 in which said solution contains a water-soluble amino acid.

11. The intermediate of claim 10 in which at least ninety percent of the aluminum is present within said first and second peaks.

12. The intermediate of claim 11 in which said aluminum chlorhydroxide has a concentration of 8 to 15% in said solution.

13. An intermediate for making a high efficacy antiperspirant composition comprising an aqueous solution of aluminum chlorhydroxide and zirconyl hydroxy chloride, the atomic ratio of Al to Zr being from 6:1 to 1:1, said intermediate produced by the process which comprises heating a 2% to 18% solution of aluminum chlorhydroxide in water at a temperature of at least 50° C. for at least two hours and adding zirconyl hydroxy chloride to said solution before, during or after said heating step in an amount to provide said atomic ratio.

14. The intermediate of claim 13 wherein said heating is conducted at 70° C. to 100° C.

15. The intermediate of claim 14 wherein said aluminum chlorhydroxide solution is at a concentration of 8 to 15% when it is heated.

16. The intermediate of claim 15 wherein said zirconyl hydroxy chloride is added after said heating step.

17. The intermediate of claim 16 in which said added zirconyl hydroxy chloride has a concentration of up to fifty-five percent in aqueous solution.

18. The intermediate of claim 16 wherein said aluminum chlorhydroxide solution is partially dried to a concentration of 45% to 55% prior to adding said zirconyl hydroxy chloride.

19. The intermediate of claim 18 wherein said intermediate, when subjected to gel permeation chromatography at a concentration of 10% on crosslinked dextran having a molecular weight exclusion range of 1000 to 30,000 for globular proteins, shows a first peak at $Kd=0.7$ and a second peak at $Kd=0.5$, the ratio of the height of said first peak to that of said second peak being at least 1.5:1, with at least 80% of the aluminum being present within said first and second peaks.

20. The intermediate of claim 14 wherein said heating is conducted for at least sixteen hours.

21. A method of making an intermediate for an antiperspirant composition having high efficacy which comprises heating a 2% to 18% solution of aluminum chlorhydroxide in water at a temperature of at least 50° C. for at least two hours and adding zirconyl hydroxy chloride to said solution before, during or after said heating step in an amount to provide an atomic ratio of Al to Zr of from 6:1 to 1:1.

22. The method of claim 21 wherein said heating is conducted at 70° C. to 100° C.

23. The method of claim 22 wherein said aluminum chlorhydroxide solution is at a concentration of 8% to 15% when it is heated.

24. The method of claim 23 wherein said zirconyl hydroxy chloride is added after said heating step.

25. The method of claim 24 wherein said aluminum chlorhydroxide solution is partially dried to a concentration of 45% to 55% prior to adding said zirconyl hydroxy chloride.

26. The method of claim 25 wherein said intermediate, when subjected to gel permeation chromatography at a concentration of 10% on crosslinked dextran having a molecular weight exclusion range of 1000 to 30,000 for globular proteins, shows a first peak at $Kd=0.7$ and a second peak at $Kd=0.5$, the ratio of the height of said first peak to that of said second peak being at least 1.5:1, with at least 80% of the aluminum being present within said first and second peaks.

27. The method of claim 22 wherein said heating is conducted for at least sixteen hours.

28. An intermediate for making an antiperspirant composition having high efficacy, said intermediate comprising an aqueous solution of aluminum chlorhydroxide and zirconyl hydroxy chloride, said solution exhibiting a peak 4 to peak 3 height ratio of at least 1:1 when subjected to gel permeation chromatography at a concentration of 10% on crosslinked dextran having a molecular weight exclusion range of 1000 to 30,000 for globular proteins.

29. The intermediate of claim 28 wherein at least 80% of the aluminum is present within said peaks 3 and 4.

30. The intermediate of claim 29 additionally comprising glycine.

31. The intermediate of claim 30 wherein said peak 4 to peak 3 height ratio is at least 1.5:1.

32. The intermediate of claim 31 wherein the atomic ratio of Al:Zr is about 1:1 to 6:1.

* * * * *